US009039879B2

(12) United States Patent
Kanao

(10) Patent No.: US 9,039,879 B2

(45) Date of Patent: May 26, 2015

(54) GAS SENSOR AND METHOD OF MANUFACTURING THEREOF

(75) Inventor: Keiji Kanao, Aichi-ken (JP)

(73) Assignee: DENSO CORPORATION, Kariya (JP)

(*) Notice: Subject to any disclaimer, the term of this patent is extended or adjusted under 35 U.S.C. 154(b) by 685 days.

(21) Appl. No.: 12/254,298

(22) Filed: Oct. 20, 2008

(65) Prior Publication Data

US 2009/0101503 A1 Apr. 23, 2009

(30) Foreign Application Priority Data

Oct. 18, 2007 (JP) ................................ 2007-271585
Sep. 8, 2008 (JP) ................................ 2008-230168

(51) Int. Cl.
*G01N 27/26* (2006.01)
*G01N 27/407* (2006.01)
*G01N 27/406* (2006.01)

(52) U.S. Cl.
CPC .......... *G01N 27/407* (2013.01); *G01N 27/4062* (2013.01)

(58) Field of Classification Search
CPC ......................... G01N 27/407; G01N 27/4062
USPC ................................. 204/421–429; 73/31.05
See application file for complete search history.

(56) References Cited

U.S. PATENT DOCUMENTS 5,246,562 A * 9/1993 Weyl et al. .................... 204/424
5,804,050 A * 9/1998 Hayakawa et al. ........... 204/424
2001/0025522 A1* 10/2001 Kojima ........................ 73/31.05
2002/0148280 A1* 10/2002 Weyl et al. .................. 73/31.05
2004/0040370 A1 3/2004 Kojima
2006/0288759 A1* 12/2006 Okumura et al. ............ 73/31.05

FOREIGN PATENT DOCUMENTS

EP 0506897 12/1995
JP 11-190716 7/1999
JP 2004-503773 2/2004
JP 2004-093306 3/2004

OTHER PUBLICATIONS

Japanese Office Action dated Nov. 17, 2009, issued in corresponding Japanese Application No. 2008-230168, with English translation.

* cited by examiner

*Primary Examiner* — Keith Hendricks
*Assistant Examiner* — Kourtney S Carlson
(74) *Attorney, Agent, or Firm* — Nixon & Vanderhye P.C.

(57) ABSTRACT

In a gas sensor sensing a specific gas component contained in gas to be measured, oxygen ion conductive solid electrolyte is used in a sensing element for sensing the specific gas component. A terminal unit is used, which comprises a pair of insulators, each having an inner side surface, disposed to pinch and hold the base end portion of the sensing element on the pair of electrode-mounted surfaces of the sensing element. The terminal unit comprises two pairs of metal terminals and a spring member. The metal terminals electrically contact electrode pads of the sensing element, pair by pair, respectively, and are disposed on the inner side surfaces of the insulators. The spring members press the pair of insulators at one or more positions of electrode-mounted surfaces of the sensing element in a width direction so that the insulators are pressed to be opposed to each other.

10 Claims, 19 Drawing Sheets

A
1
21 316 31 23 32 33
32
333
21
310
22
322
2
32
322
333
33 310 32 316 23 21 31
TH
WD
A

GAS SENSOR AND METHOD OF MANUFACTURING THEREOF

CROSS REFERENCES TO RELATED APPLICATION

The present application relates to and incorporates by reference Japanese Patent Applications No. 2007-271585 filed on Oct. 18, 2007 and No. 2008-230168 filed on Sep. 8, 2008.

BACKGROUND OF THE INVENTION

1. Technical Field

The present invention relates to a gas sensor used for detecting the concentration of a specific gas (gas component) contained in a gas to be measured and a method of manufacturing the gas sensor, and in particular to the gas sensor provided with an oxygen ion conductive solid electrolyte member.

2. Related Art

There has been known a gas sensor for detecting the concentration of a specific gas (i.e., gas component) contained in a gas to be measured, such as an exhaust gas from cars.

This kind of gas sensor is exemplified by EP patent application publication No. 0506897, A gas sensor disclosed by this publication is provided with a cell having electrodes on both sides of an oxygen ion conductive solid electrolyte member and an sensing element integrally having a heater equipped with a heat generating device heating the cell. The sensing element has a base end portion on which there are two pairs of electrode pads electrically connected to the heat generating device and the electrodes, respectively. Practically, the sensing element has two approximately parallel electrode-mounted surfaces, and, of the four electrode pads, two electrode pads are fixedly arranged at two given positions of each electrode-mounted surface, which are aligned in the width direction of each electrode-mounted surface.

The above configuration of the gas sensor is exemplified in FIG. 22, in which there is provided a sensing element 92 having a base end portion 922 at which two electrode-mounted surfaces 923 are formed back to back. As shown, two metal pads 921 are secured on each electrode-mounted surface 923. The metal pads 921 come in contact with metal terminals 932 connected to external lead wires. A pair of base-side insulators 931 has Inner side surfaces to be opposed to each other, on each of which the two metal terminals 932 are secured so as to touch the two metal pads 921 respectively. The base end portion 922 of the sensing element 92 is pinched (gripped) between the two paired base-side insulators 931. A spring member 933, which is shaped into an approximately annular form, is placed to press the paired base-side insulators 931 so that each of the insulators 931 is pressed inwardly. This pressing allows the two pairs of metal terminals 932 are forcibly touched to the two pairs of electrode pads 921.

However, the use of the annular spring member 933 often results in uneven pressing force applied to the one pair of electrode pads 921 arranged in the width direction of each electrode-mounted surface 923. In such a case, it is difficult to give even contact pressure from the four metal terminals 932 to the four electrode pads 921.

In particular, in cases where both electrode-mounted surfaces 923 of the sensing element 92 have a lower parallelism, the metal terminals have irregularities in their thicknesses, or the paired base-side insulators 931 are uneven in their shapes, it is difficult to have even contact pressure of the electrode pads 921 to the metal terminals 932.

Such irregularities in the contact pressure will cause irregularities in contact resistance between each electrode pad 921 and so each metal terminal 932. Thus, detection accuracy of cells in the sensing element 92 may be reduced and/or activation time of the cells may be delayed.

SUMMARY OF THE INVENTION

The present invention has been made in consideration of the foregoing difficulties and an object of the present invention is to provide a gas sensor that has the capability of equalizing the contact pressure of the metal terminals to the electrode pads or lessening irregularities in the contact pressure thereof, and a method of manufacturing such gas sensors.

In order to achieve the above object, the present invention provides as one aspect a gas sensor comprising: a sensing element i) providing an axial direction in one end of which a base end portion is provided and providing a width direction perpendicular to the axial direction, ii) a cell composed of an oxygen ion conductive solid electrolyte member, iii) a pair of electrode-mounted surfaces formed to be back to back and parallel with each other in the width direction, and iv) a heater to heat the cell, the cell being integrally assembled with the heater; an insulator through which the sensing element is inserted and held; a housing fixedly containing the insulator placed to be inserted through the housing; two pairs of electrode pads secured on the pair of electrode-mounted surfaces of the sensing element in the base end portion so as to allow the electrode pads to provide electrical connections for heating the cell and for detecting a concentration of a specific gas to be measured, pair by pair, respectively, wherein two of the electrode pads are disposed on each electrode-mounted surface separately at intervals in the width direction; and a terminal unit comprising a pair of insulators, each having an inner side surface, disposed to pinch and hold the base end portion of the sensing element on the pair of electrode-mounted surfaces of the sensing element, two pairs of metal terminals electrically contacting the electrode pads, pair so by pair, respectively, and being disposed on the inner side surfaces of the insulators, and a spring member pressing the pair of insulators at one or more positions of the electrode-mounted surfaces of the sensing element in the width direction so that the insulators are pressed to be opposed to each other.

As another aspect, the present invention provides a method of manufacturing a gas sensor comprising: a sensing element i) providing an axial direction in one end of which a base end portion is provided and providing a width direction perpendicular to the axial direction, ii) a cell composed of an oxygen ion conductive solid electrolyte member, iii) a pair of electrode-mounted surfaces formed to be back to back and parallel with each other in the width direction, and iv) a heater to heat the cell, the cell being integrally assembled with the heater; an insulator through which the sensing element is inserted and held; a housing fixedly containing the insulator placed to be inserted through the housing; and two pairs of electrode pads secured on the pair of electrode-mounted surfaces of the sensing element in the base end portion so as to allow the electrode pads to provide electrical connections for heating the cell and for detecting a concentration of a specific gas to be measured, pair by pair, respectively, wherein two of the electrode pads are disposed on each electrode-mounted surface separately at intervals in the width direction, the manufacturing method comprising steps of: preparing in advance a terminal unit comprising a pair of insulators, each having an inner side surface, disposed to pinch and hold the base end portion of the sensing element on the pair of electrode-mounted surfaces of the sensing element, two pairs of metal terminals electrically contacting the electrode pads, pair by pair, respectively, and being disposed on the inner side surfaces of the insulators, and a spring member pressing the pair of insulators at one or more positions of the electrode-mounted surfaces of the sensing element in the width direction so that the insulators are pressed to be opposed to each other; separating the paired insulators by applying a separating force against a pressure force of the spring member until there is formed a gap between the two pairs of metal terminals, the gap being larger than a thickness between the electrode-mounted surfaces of the base end portion of the sensing element; inserting the base end portion of the sensing element into the gap; and releasing the separating force so that, with the two pairs of metal terminals made to contact the electrode pads, the base end portion of the sensing element is fixedly gripped by the terminal unit.

BRIEF DESCRIPTION OF THE DRAWINGS

In the accompanying drawings.

DETAILED DESCRIPTION OF PREFERRED EMBODIMENTS (First Embodiment)

Referring to FIGS. 1-18, a gas sensor and a method of manufacturing the same according to a first embodiment of the present invention will now be described.

Figure 1:
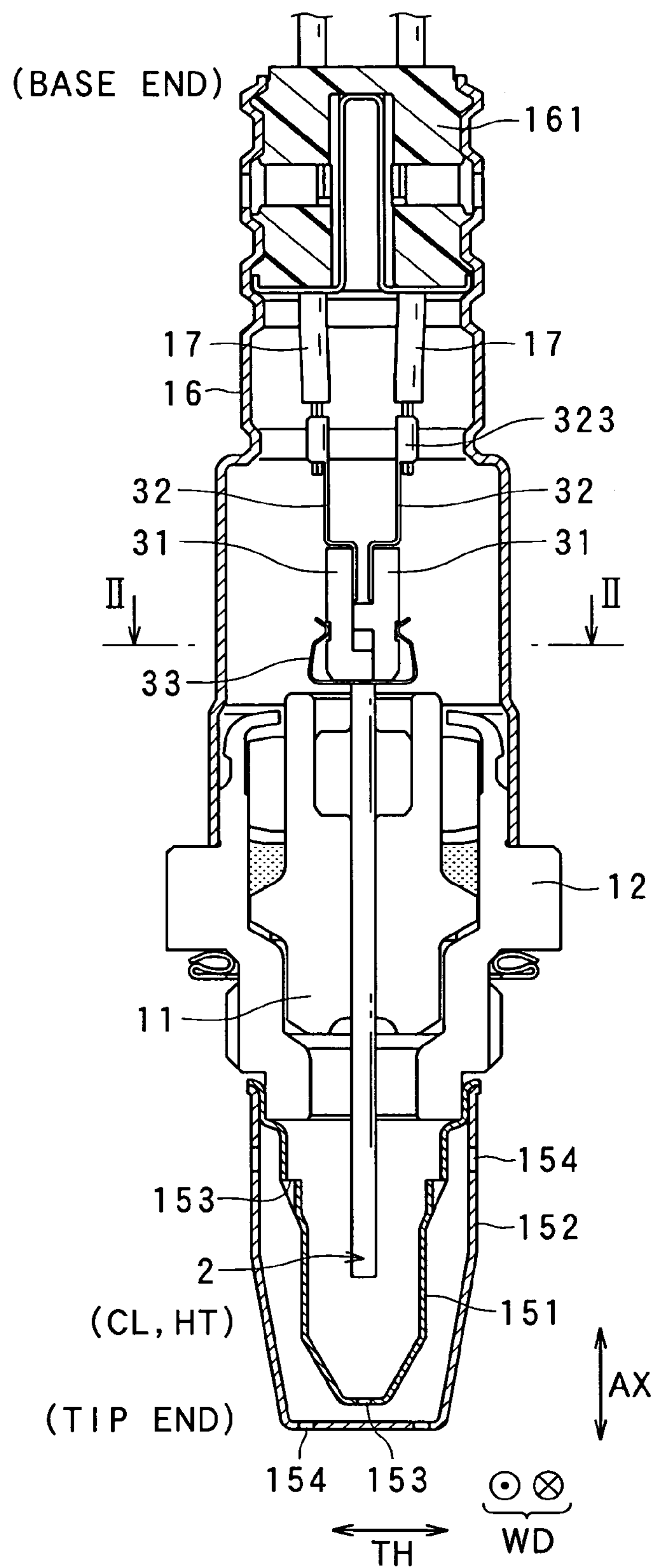
FIG. 1 is an axial sectional view of a gas sensor according to a first embodiment of the present invention, the axial sectional view being along an axial direction provided by the gas sensor.

FIG. 1 shows a gas sensor 1 according to the first embodiment. The gas sensor is provided with a sensing element 2 and an insulator 11 that holds the sensing element 2 inserted therethrough, and a housing 12 that holds the insulator (insulating member) 11 inserted therethrough. The sensing element 2, which has been known, comprises a cell CL (not shown in detail) composed of an oxygen ion conductive solid electrolyte member having electrodes disposed on both sides of the electrolyte member, and a heater HT (not shown in detail) having a heating device that heats the cell. The cell CL is integrally produced with the heater. Accordingly, the sensing element 2 is able to sense a specific gas component contained in gas to be measured, such as exhaust gas, and outputs an electric signal via signal electrodes to provide an external processor with the sensed results.

Figure 2:
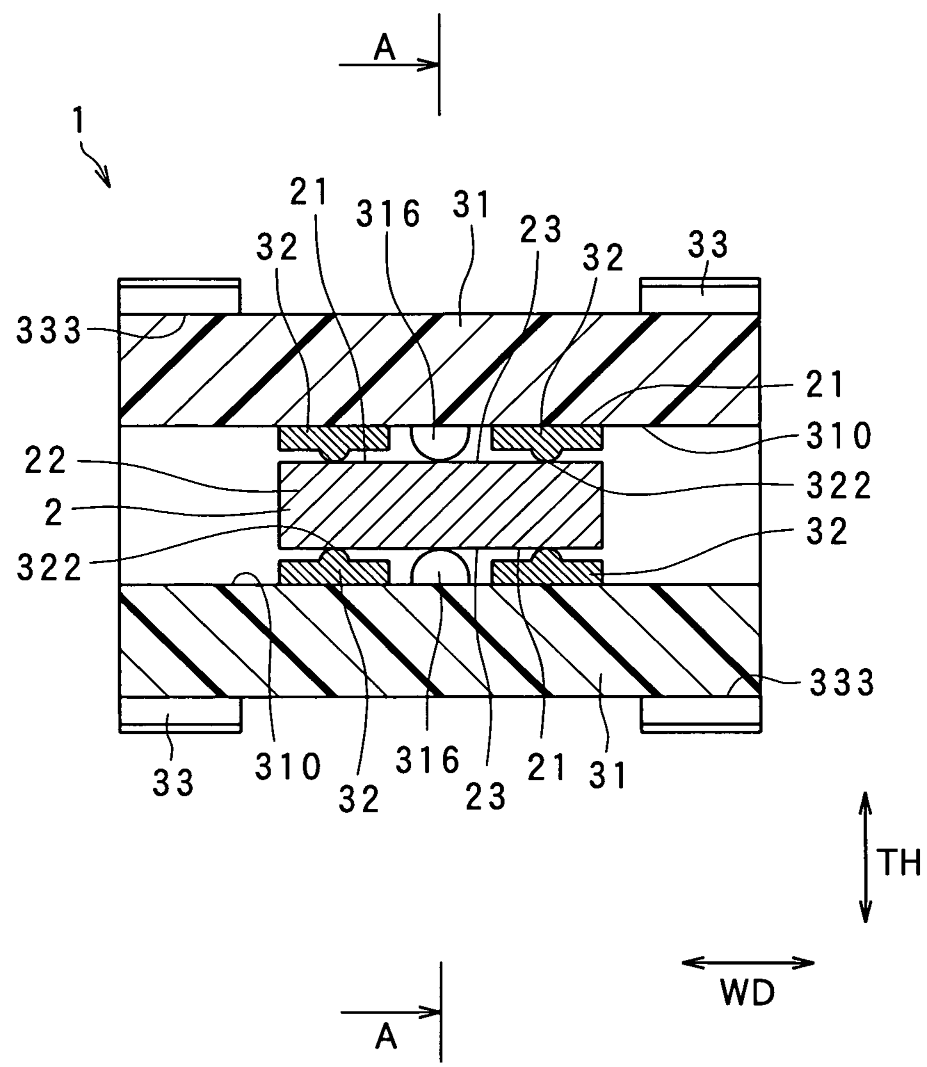
FIG. 2 is a sectional view of a terminal unit employed by the gas sensor, which is taken along a II-II line in FIG. 1, where the terminal unit grips a sensing element and the sectional view is perpendicular to the axial direction.
Figure 3:
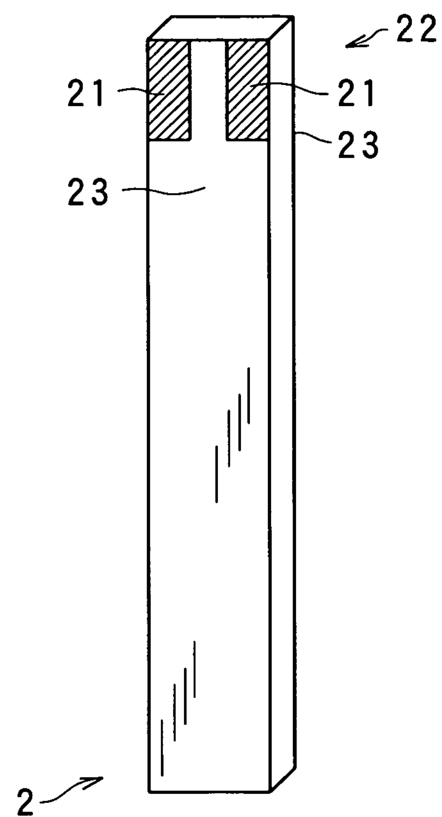
FIG. 3 is a perspective view showing the sensing element.

As shown in FIGS. 2 and 3, the sensing element 2 comprises two pairs of electrode pads 21 respectively, pair by pair, electrically connected to the heater HT and electrodes of the cell CL. The sensing element 2 has a base end portion 22 formed with two electrode-mounted surfaces 23 which are back to back and substantially parallel with each other, On the electrode-mounted surfaces 23, the two pairs of electrode pads 21 are securely mounted. Of those four electrode pads 21, two electrode pads 21 are mounted on each electrode-mounted surface 23 such that they are located in a width (lateral) direction WD of each electrode-mounted surface 23. The width direction WD is the lateral direction in FIG. 2.

Figure 12:
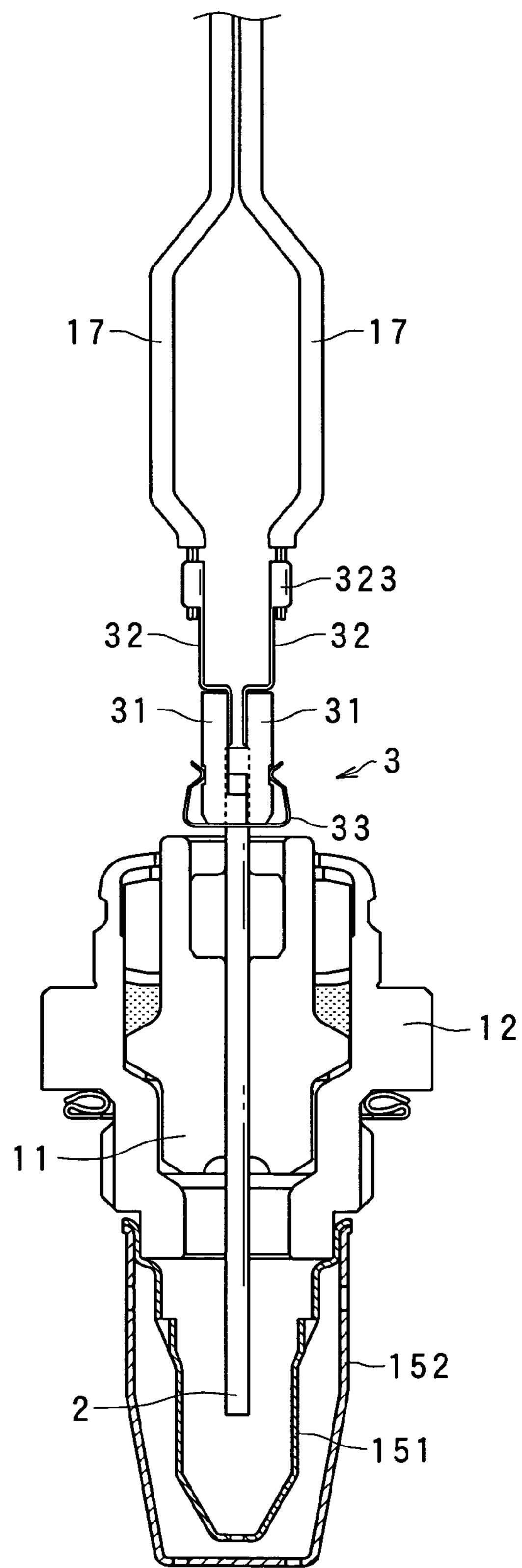
FIG. 12 illustrates both the sensing element and the terminal unit, which is seen after mutually assembling thereof.

As shown in FIGS. 2 and 12, the base end portion 22 of the sensing element 2 is grasped by a terminal unit 3. This terminal unit 3 comprises a signal pair of bases-side insulators 31 and four (two pairs of) metal terminals 32, and four (two pairs of) spring members 33. The single pair of base-side insulators 31 are arranged to securely pinch (grip) the base end portion 22 of the sensing element 2 between the pair of electrode-mounted surfaces 23. Every two of the four metal terminals 32 are secured on an inner side surface 310 of each base-side insulator 31 at intervals in the width direction WD so that each metal terminal 32 comes in contact with each electrode pad 21. The spring members 33 are disposed to push the pair of base-side insulators 31 so that the base-side insulators 31 become closer to each other. Of the spring members 33, every two spring members are arranged at intervals in the width direction WD so as to touch the outer side surface of each base-side insulator 31.

Figure 9:
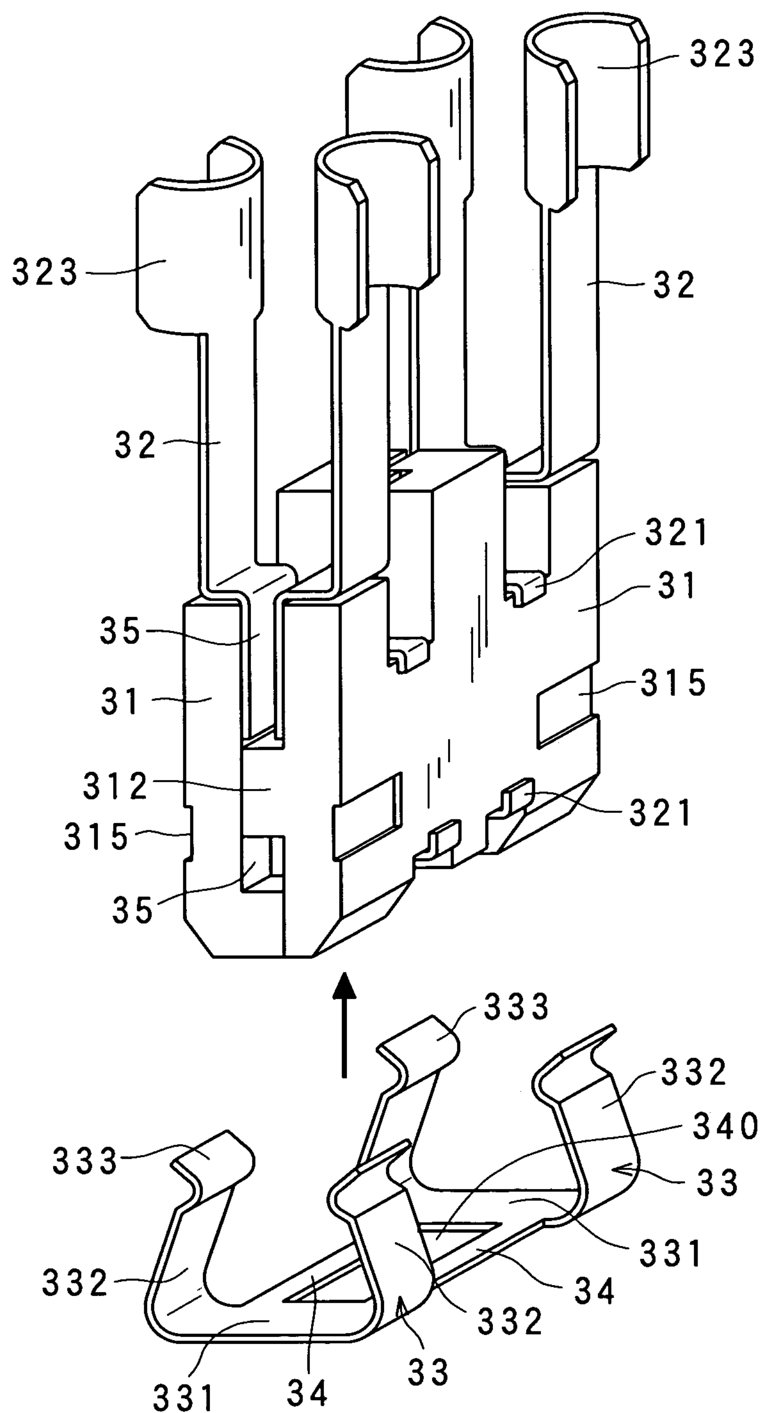
FIG. 9 is a perspective view showing the pair of base-side insulators each assembled with metal terminals and mutually combined together.

The spring members 33 are also illustrated in FIG. 9, in which the four spring members 33 are mutually united as a single device by a connecting member 34. Each spring member 33 is a blade spring, which comprises a flat planar base part 331, a pair of rising parts 332 is each rising from an end of the base part 331 and inwardly being bent, and contact parts 333 each being formed at the tip of each rising part 332 so as to contact to base-side insulator 31. The connecting member 34 is composed of two members both mutually connecting the two planar base parts 331 of the respective spring members 33 at both ends of each planar base part 331, respectively. The two connecting members 34 are mutually separated to form an opening 340 through which the sensing element 2 is inserted.

In FIGS. 9, 10, 13 and 14, the terminal unit 3 comprises a plurality of side-opened recesses 35 respectively opening in different two directions which are parallel to the electrode-mounted surfaces 23 and perpendicular to the axial direction AX of the sensing element 2. The side-opened recesses 35 are located between the paired base-side insulators 31.

Figure 5:
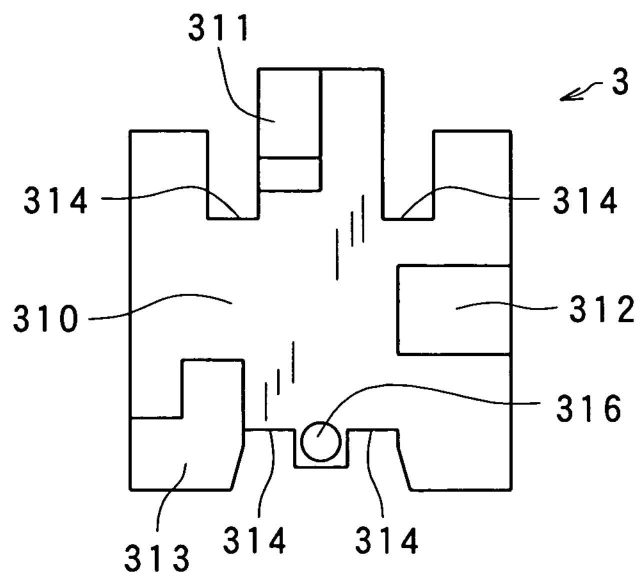
FIG. 5 is a plan view showing the base-side insulator.
Figure 6:
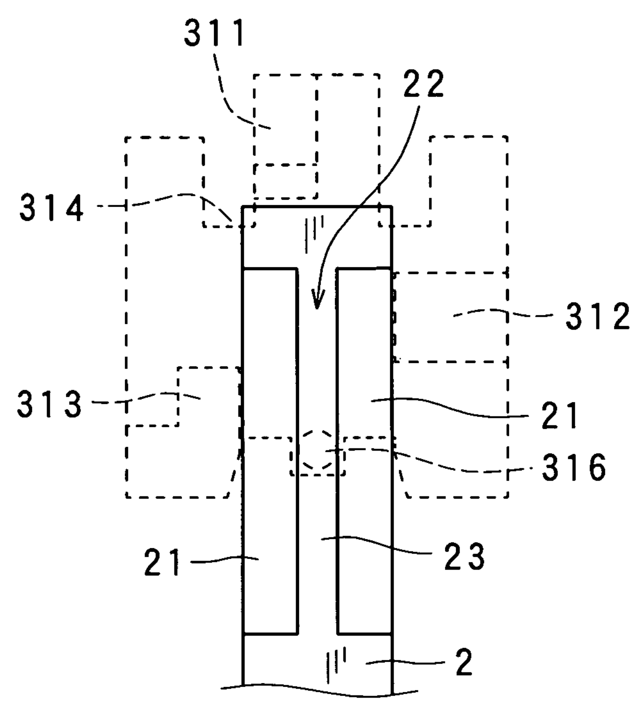
FIG. 6 is a plan view showing the sensing element assembled with the base-side insulator.

As shown in FIGS. 5 and 6, each base-side insulators 31 so comprises a first positioning part 331, a second positioning part 312, and a third positioning part 313, which are protruded from its inner side surface 310, for positioning the base end portion 22 of the sensing element 2. The first positioning part 311 is for positioning the base end of the sensing element 2, while the second and third positioning parts 312 and 313 are for both edges of the base end portion 22 in the width direction WD The first to third positioning parts 311 to 313 are located at positions of the base-side insulator 31, which are not asymmetric to each other in the width (lateral) direction WD.

Figure 8:
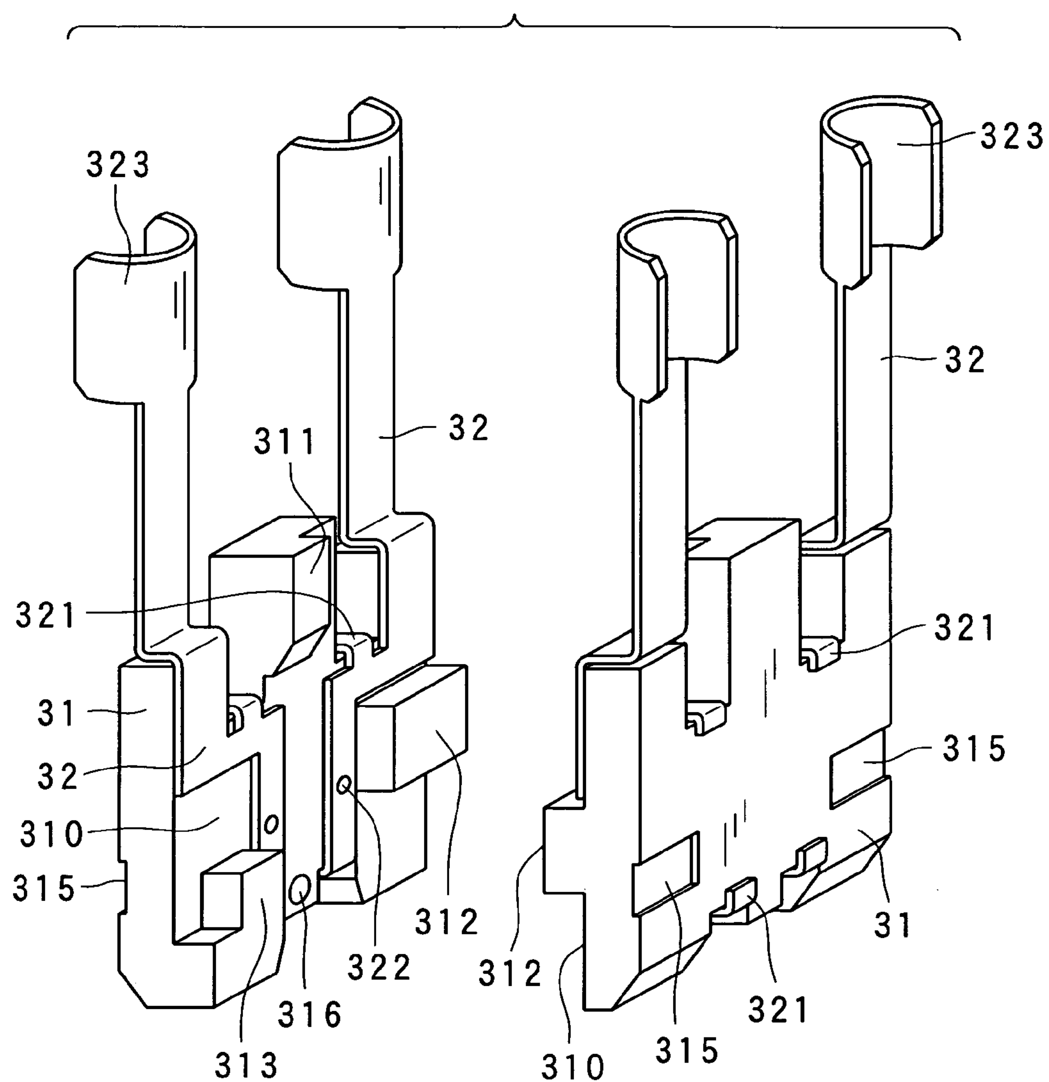
FIG. 8 is a perspective view showing a pair of base-side insulators each assembled with metal terminals.

In addition, as shown in FIG. 8, the metal terminals are securely arranged on and along parts of the inner side surface 310 of the base-side insulator 31, where the first to third positioning parts 311 to 313 are not present at those parts of the inner side surface 310.

Figure 4:
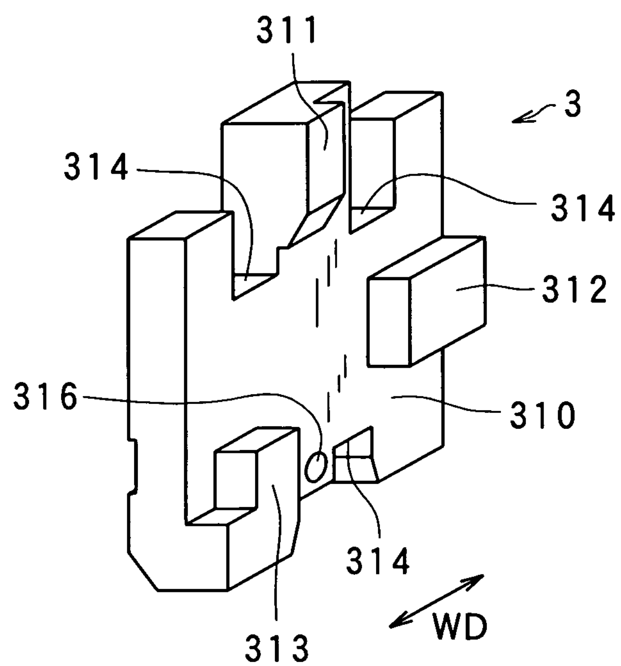
FIG. 4 is a perspective view showing a base-side Insulator employed by the gas sensor.

As shown in FIGS. 4 and 5, each base-side insulator 31 has a tip end portion as well as the foregoing base end portion, and there are two cut portions 314 at each of the base and tip end portions. Each terminal plate 31 has two engaging portions 31, which engage with two of the is cut portions 34, which are illustrated in FIG. 8.

As shown in FIGS. 8 and 9, each base-side insulator 31 has a rear surface, on which there are formed two recesses 315. Hence the two base-side insulators 31 provide the four recesses 315 in total, so that the four contact parts 333 of the spring member members 33 can be seated on the four recesses 315 for realizing tight contact thereto.

Each of the metal terminals 32 comprises, as shown in FIGS. 2 and 8, a protruding contact part 322 that faces the contact parts of the sensing element 2. As can be understood from FIGS. 8 to 12, each metal terminal 32 comprises a lead connecting portion 323 which is to be electrically connected to external lead wires 17. The lead connecting portions 323 are located close to the base end side more than the base-side insulator 31. The electrical connection between each lead connecting portion 323 and each external lead wire 17 is made by wrapping and caulking the external lead wire 17 around and to the lead connecting portion 323.

Figure 7:
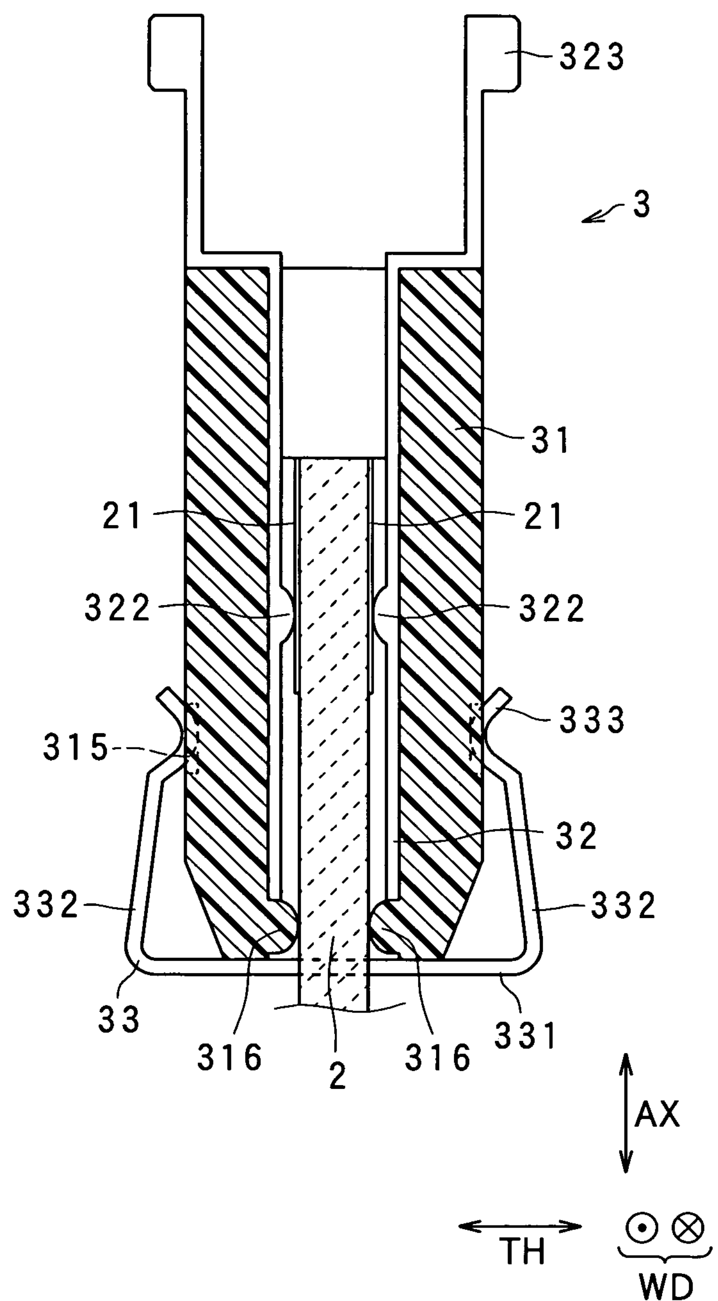
FIG. 7 is a sectional view taken along an A-A line in FIG. 2.

Further, each base-side insulator 31 has, as shown in FIGS. 2 and 4-7, an insulative protrusion 316 that protrudes toward the sensing element 2. The contact between each protruding contact part 322 and each electrode pad 21 and the contact between each insulative protrusion 316 and the sensing element 2 are shifted from each other in the axial direction AX of the sensing element 2, as shown in FIG. 7. Hence, at the axial positions where the contacts are made between each protruding contact part 322 and each electrode pad 21 and each insulative protrusion 316 and the sensing element 2, the spring member 33 is able to press the pair of base-side insulators 31 so that the two insulators 31 are pressed mutually inwardly in a thickness direction TH perpendicular to the width direction WD.

The gas sensor 1 further comprises, as shown in FIG. 1, an inner element cover 151 and an outer element cover 152 both of which are secured on the tip end of the housing 12 so as to doubly cover the tip end portion of the sensing element 2. The inner and outer element covers 151 and 152 have air holes 153 and 154, respectively, for introducing a specific gas to be detected.

The housing 12 has also a base end, on which a substantially cylindrical base-side cover 16 is bonded, which contains the terminal unit 3, as illustrated in FIG. 1. This base-side cover 16 has a base end portion closed by a rubber bush 161, through which the external lead wires 17 pass in an air-tight manner.

Figure 10:
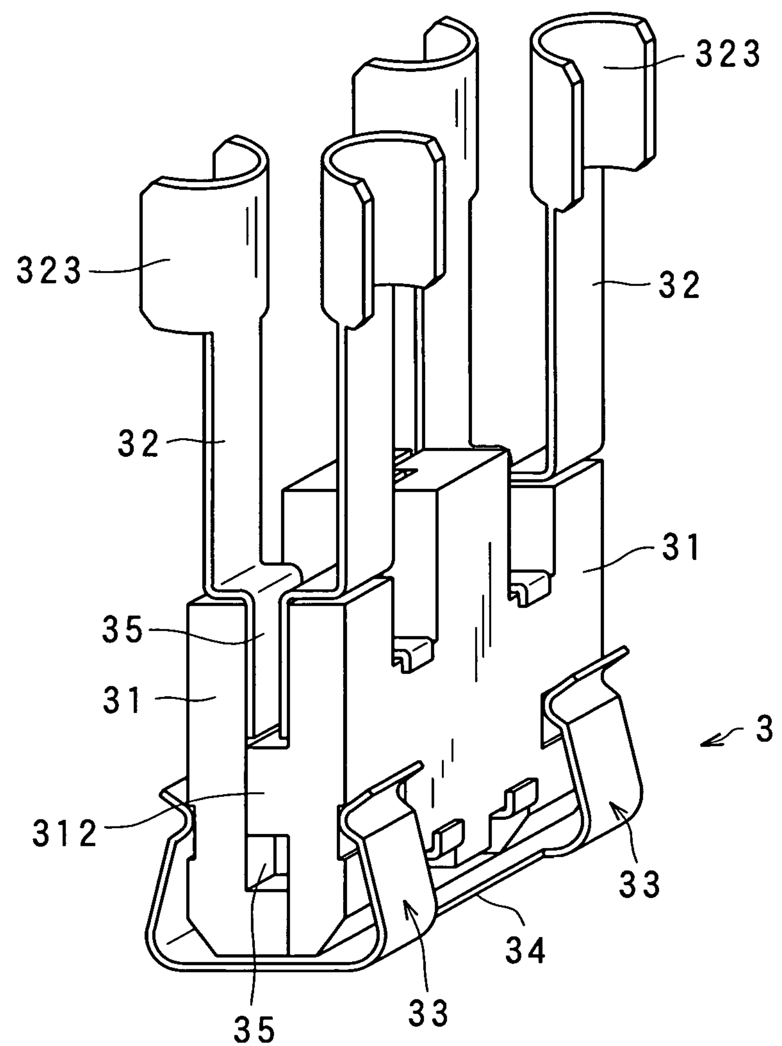
FIG. 10 is a perspective view of the terminal unit.

In manufacturing the gas sensor 1 according to the present embodiment, the terminal unit 3 is first assembled, as shown in FIGS. 8-10.

Practically, as illustrated in FIG. 8, the two metal terminals 32 are attached to each of the pair of base-side insulators 31.

In the next step shown in FIG. 9, the two base-side insulators 31, to which the metal terminals have been attached, are combined to each other so as to the inner side surfaces 310 of both base-side insulators 31 are opposed to each other.

In the next step shown in FIG. 10, the unified two spring members 33 are fit to the pair of combined base-side insulators 31 from the tip end portion thereof, so that the spring members 33 can hold the base-side insulators 31 therein. In this held state, the contact parts 333 of the spring members 33 are made to securely touch the recesses 315 of the base-side insulators 31. In this way, the terminal unit 3 is assembled.

Figure 14:
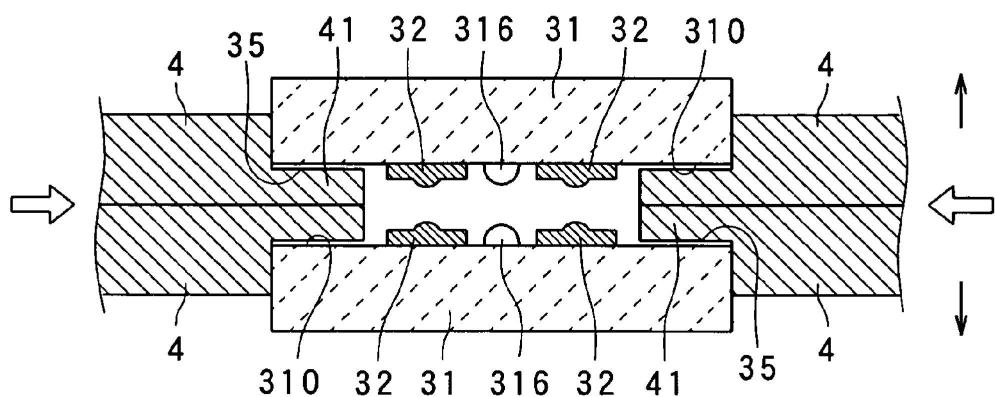
FIG. 14 is a sectional view showing a state where the separating jigs are inserted into side-opened recesses of the terminal unit.
Figure 15:
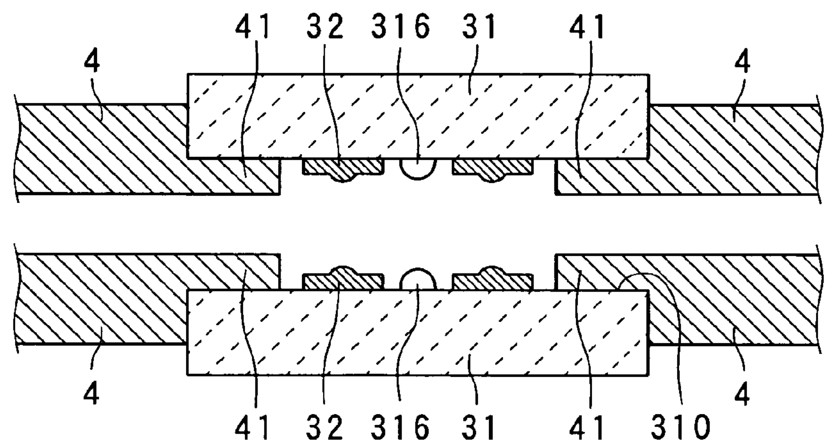
FIG. 15 is a sectional view showing a state where the separating jigs are expanded to expand the distance between the metal terminals of the terminal unit.

In the next step, as shown in FIGS. 14 and 15, the pair of base-side insulators 31 of the terminal unit 3 is subjected to an application of a separating force against the pressing force of the spring members 33. The separating force is shown by arrows A1 in FIG. 14. This separation using the separating force is performed until a spatial gap larger than the thickness between the paired electrode-mounted surfaces 23 at the base end portion 22 of the sensing element 2 is produced between the two pairs of metal terminals 32.

Figure 16:
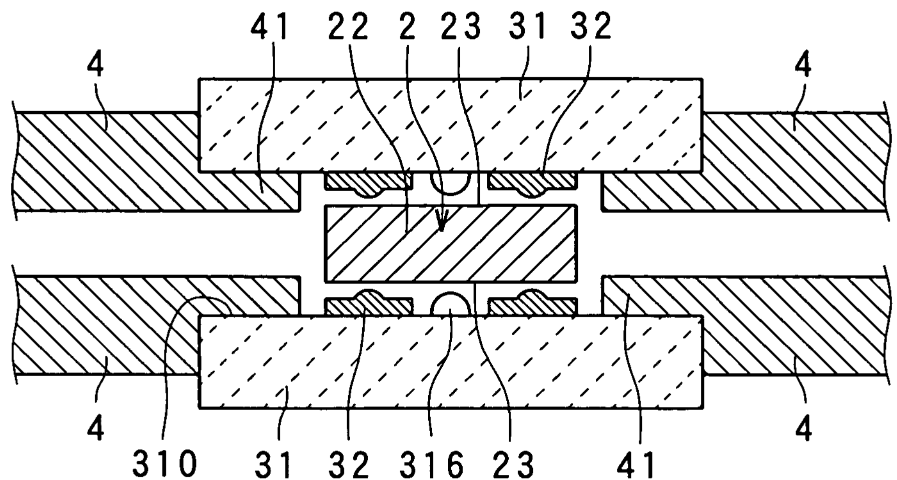
FIG. 16 is a sectional view showing a state where the base end portion of the sensing element is inserted into the expanded space between the metal terminals of the terminal unit.

Then, as shown in FIG. 16, the base end portion 22 of the sensing element 2 is inserted into the space produced between the two pairs of metal terminals 32.

Figure 17:
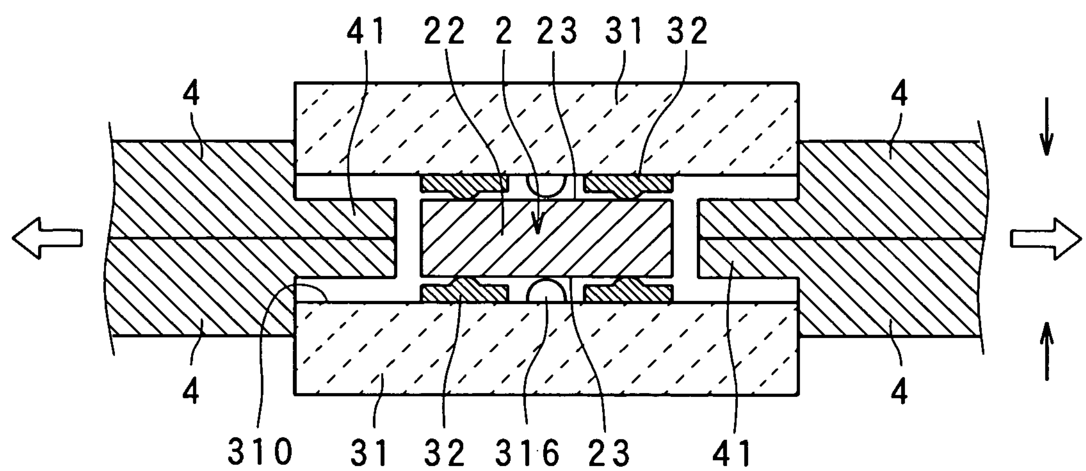
FIG. 17 is a sectional view showing a state where the terminal unit fixedly grippes the base end portion of the sensing element.

In the next step, the separating force which has been applied to the pair of base-side insulators 31 is released, so that the pressing force of the spring members 33 becomes effective, as shown by arrows A2 in FIG. 17. Hence, with the two pairs of metal terminals 32 made to touch the electrode pads 21 of the sensing element 2, its base end portion 22 is held by the terminal unit 3 in a gripping manner.

Figure 11:
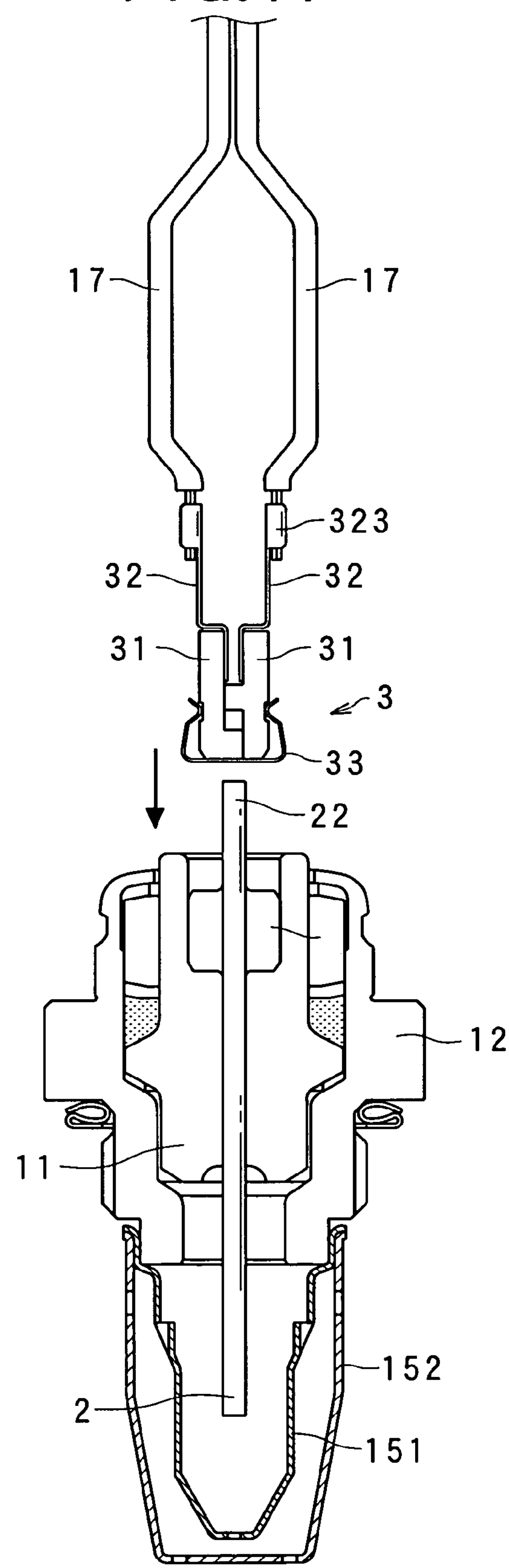
FIG. 11 illustrates both the sensing element and the terminal so unit, which is seen before mutually assembling thereof.

Further, as shown in FIGS. 11 and 12, in the state where the sensing element 2 is inserted and held through the insulator 11 held by the housing 11, the terminal unit 3 is attached to the base end portion 22 of the sensing element 2.

In applying the separating force to the pair of base-side insulators 31, as shown in FIGS. 13-17, a pair of separating jigs 4 is inserted into each side-opened recess 35 of the terminal unit 3, as so shown in FIGS. 13-17. Then, operating the separating jigs 4 makes it possible to separate the pair of base-side insulators.

Figure 13:
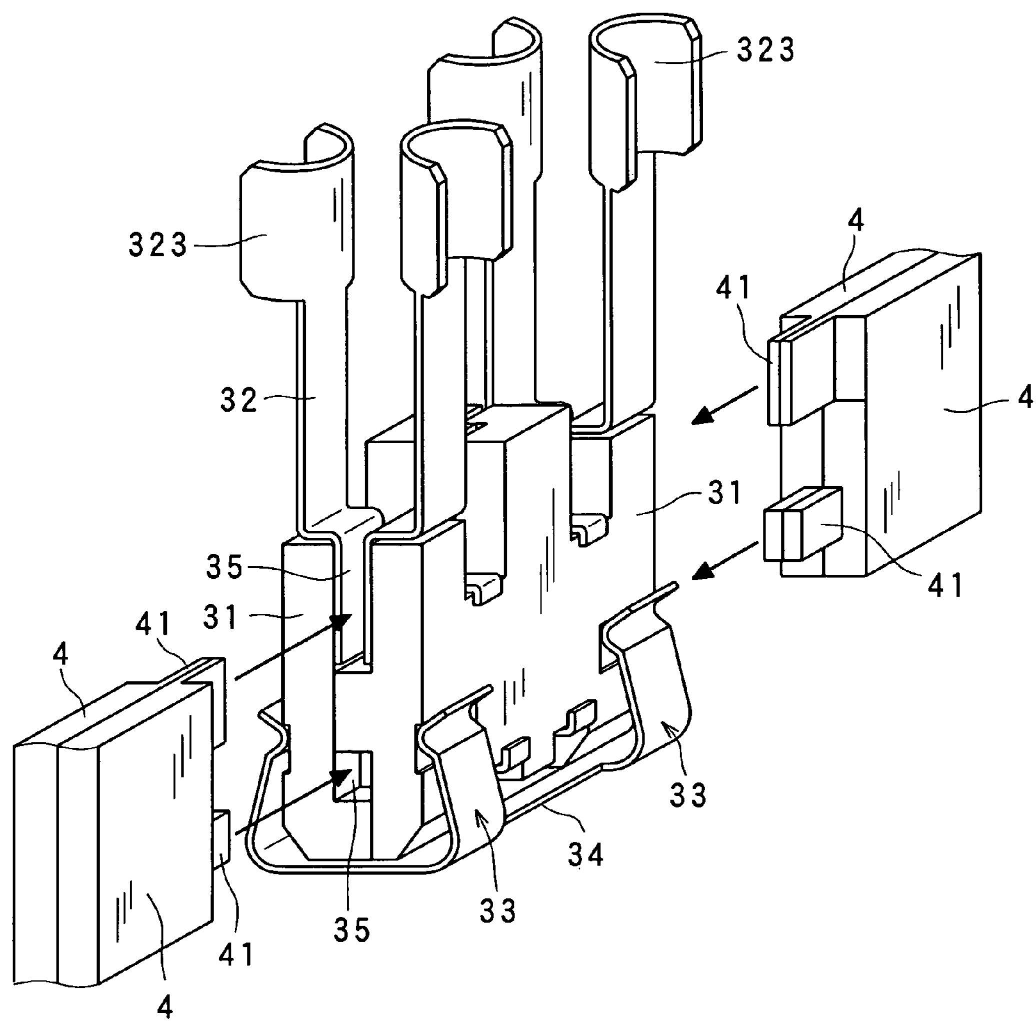
FIG. 13 is a perspective view showing a state where separating jigs are to be arranged to both sides of the terminal unit in the first embodiment.

That is, as shown in FIGS. 13 and 14, the terminal unit 3 is provided with the side-opened recesses 35, which are opened from the respective sides of the terminal unit 3 in the width direction. The side-opened recesses 35 are four in total and are two in each side of the terminal unit 3. In each side of the terminal unit 3, each of the two side-opened recesses 35 is formed between the paired base-side insulators 31. Depending on the axial positions of the side-opened recesses 35, the two pairs of separating jigs 4 each having inserting ends 41 corresponding to such axial positions are prepared.

As shown in FIG. 13, each pair of separating jigs 4, of which inserting ends 41 are closed to each other, is set in front of each side of the terminal unit 3. Then, as shown in FIG. 14, the closed inserting ends 41 are inserted into each side-opened recess 35 of the terminal unit 3 (refer to arrows B1 in FIG. 14).

Then, as shown in FIG. 15, each separating jig 4 is operated to open its inserting ends from one the other. Hence, the base-side insulators 31, to which the inserting ends are attached forcibly, are separated from each other, so that the space between the metal terminals 32 secured on the respective insulators 31 is expanded. This expansion is made to make the space larger than the base end portion 22 of the sensing element 2.

As shown in FIG. 16, into the space between the base-side Insulators 31 which have been expanded, the base end portion 22 of the sensing element 2 is then inserted.

Then, each pair of separating jigs 4 are closed, as shown in FIG. 17. Consequently, the base end portion 22 of the sensing element 2 is just fixedly gripped or clipped by the base-side insulators 31, whereby the metal terminals 32 on the insulators 31 is made to electrically contact the electrode pads 21 on the sensing element 2 in a tight manner.

Next the separating jigs 4 are then retreated to be withdrawn from the terminal unit 3 (refer to arrows B2 in FIG. 17), so that the inserting ends 41 of the jigs 4 are pulled out of the side-opened recesses 35.

In this way, the terminal unit 3 is fixedly pinched in the base end portions 22 of the sensing element 2.

After the above assembly, the base-side cover 16 is bonded to the base side of the housing 12, whereby the terminal unit 3 and the other components are enclosed by the housing 12, completing the assembly of the gas sensor 1.

Figure 18:
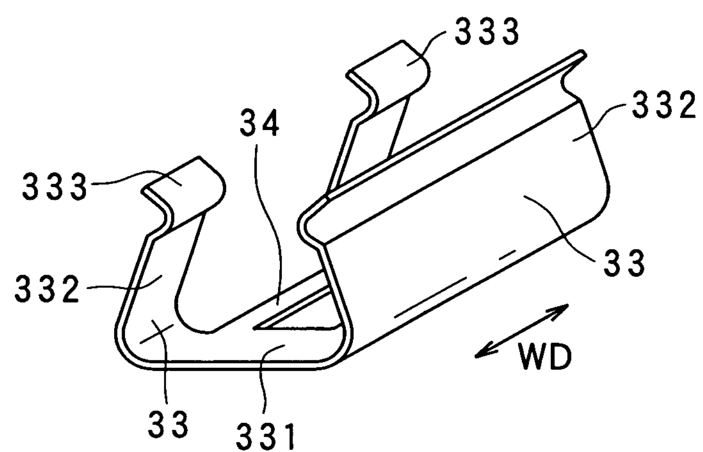
FIG. 18 is a perspective view showing a spring member is according to a modification of the first embodiment.

In the first embodiment, the shape of the spring members 33 is not always limited to the foregoing one, but may be modified into other modes. For example, as shown in FIG. 18, of the two spring members 33, one rising part of one pair of rising parts 332 and one contact part of one pair of contact parts 333 are composed by one member.

The advantageous effects of the gas sensor 1 according to the present embodiment will now be described.

The plural spring members 33 are placed to press the pair of base-side insulators 31 at the plural positions of the electrode-mounted surface 23 in the width direction WD. Thus, the two metal terminals 32 secured on the inner side surface 310 of each base-side insulator 31 can be made to contact, respectively, at even or approximately even contact pressure, the two electrode pads 21 secured in parallel each electrode-mounted surface 23 of the base end portion 22 of the sensing element 2 in the width direction WD.

The electrode pads 21 secured on each electrode-mounted surface 23 are touched to the metal terminals 32 of the base end portion 22 of the sensing element 2 on both sides of the sensing element 2. As a result, the metal terminals 32 are made to tightly touch the electrode pads 21 on the pair of electrode-mounted surfaces 23 at even or approximately even pressure. Accordingly, the four metal terminals 32 can be touched to the four electrode pads 21, respectively, without any irregularities in pressing pressure.

Namely, even in the case where the parallelism of the pair of electrode-mounted surfaces 23 of the sensing element is low, there are irregularities in the thickness of the metal terminals 32, or the base-side insulators 31 are uneven in their shapes, the contact pressure of the metal terminals 32 to the four electrode pads 21 can be even or approximately even.

Hence, irregularities in contact resistance between the electrode pads 21 and the metal terminals 32 can be suppressed or avoided, and the contact resistance at any electrical contact point can be made sufficiently smaller. Consequently, it is possible to lessen or prevent a decrease in detection accuracy of the sensing cell and a delay or any other detection performance can be avoided from being deteriorated.

In addition, the spring members 33 press each of the paired base-side insulators 31 so as to be opposed to each other at both axial contact positions between the protruding contact parts 322 and the electrode pads 21 and axial positions between the insulative protrusions 316 and the sensing element 2. This pressure structure allows of the pressure force of the spring members 33 to be applied to the electrode pads 21 and the metal terminals 32 in a stable and reliable manner. In particular, in the present embodiment, the spring members 33 apply the pressure force to the same axial positions of the base-side insulators 31 on both thickness-directional sides thereof. This will enhance the foregoing stable and reliable pressure.

Moreover, the terminal unit 3 according to the present embodiment has the plural side-opened recesses 35 produced between the paired base-side insulators 31. The pair of separating jigs 4 are applied to the side-opened recesses 35 of each width-directional side of the terminal unit 3. The jigs 4 are inserted into the side-opened recesses 35 respectively, and are operated so as to separate the paired base-side insulators 31 from each other in the thickness direction. Hence the base end portion 22 of the sensing element 2 can easily be inserted between the two base-side insulators 31, whereby the four electrode pads 21 can come into contract with the respective four metal terminals 32 for establishing electrical connections. In this way, the terminal unit 3 can be assembled with the sensing element 2, providing an easier and reliable manufacturing technique for the gas sensor 1.

In the present embodiment, as stated, it is therefore possible to provide the gas sensor in which the electrode pads 21 are made to contact the metal terminals 32, respectively, at even or approximately even contact pressure.

In the manufacturing method of the gas sensor described above, the terminal unit is assembled, and then the paired base-side insulators are separated from each other using the separating jigs. And the base end portion 22 of the sensing element 2 is inserted into a gap formed between the base-side insulators 31 such that the metal terminals 32 are forcibly touched to the base end portion 22, that is, to the electrode pads 21, respectively. Hence, it is possible to easily assemble the sensing element 2 with the terminal unit 3.

The gas sensor to be manufactured according to the present manufacturing method is able to allow the metal terminals 32 to touch the electrode pads 21 at even contact pressure. This is thanks to the spring members 33 that press the paired base-side insulators at two positions separated at intervals in the width direction WD.

In this way, the manufacturing method according to the present embodiment makes it possible to manufacture the gas sensor in which all the metal terminals 32 are made to contact, respectively, all the electrode pads 21 at even or approximately even contact pressure.

(Second Embodiment)

Figure 19:
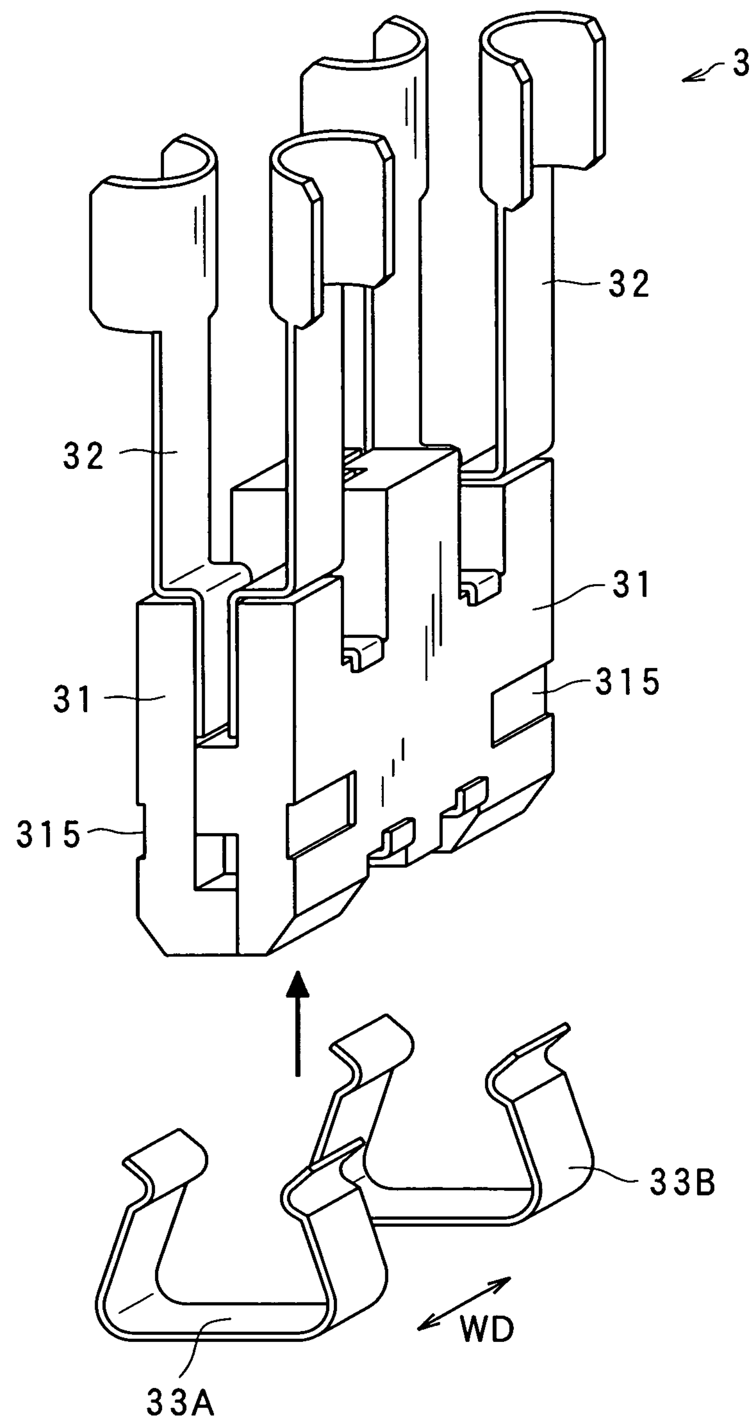
FIG. 19 is a perspective view showing a terminal unit and a spring member both of which are according to a second embodiment of the present invention.

Referring to FIG. 19, a gas sensor according to a second embodiment of the present invention will now be described. In the second embodiment, the same or identical components as or to those in the first embodiment will be given the same reference numerals for the sake of simplifying or omitting the description. This way of description is true of the succeeding embodiments.

A gas sensor according to the present embodiment has the configuration shown in FIG. 19, where the terminal unit 3 includes mutually separated two spring members 33A and 33B which press the paired base-side insulators 31.

That is, unlike the spring members 33 physically connected by the connecting member 34, which is shown in the first embodiment (refer to FIG. 9), the mutually independent two spring members 33A and 33B are used to be arranged in the width direction WD.

The remaining configurations in the second embodiment are the same as those in the first embodiment. The configurations in the second embodiment are thus able to provide the similar advantageous operations to those in the first embodiment.

(Third Embodiment)

Figure 20:
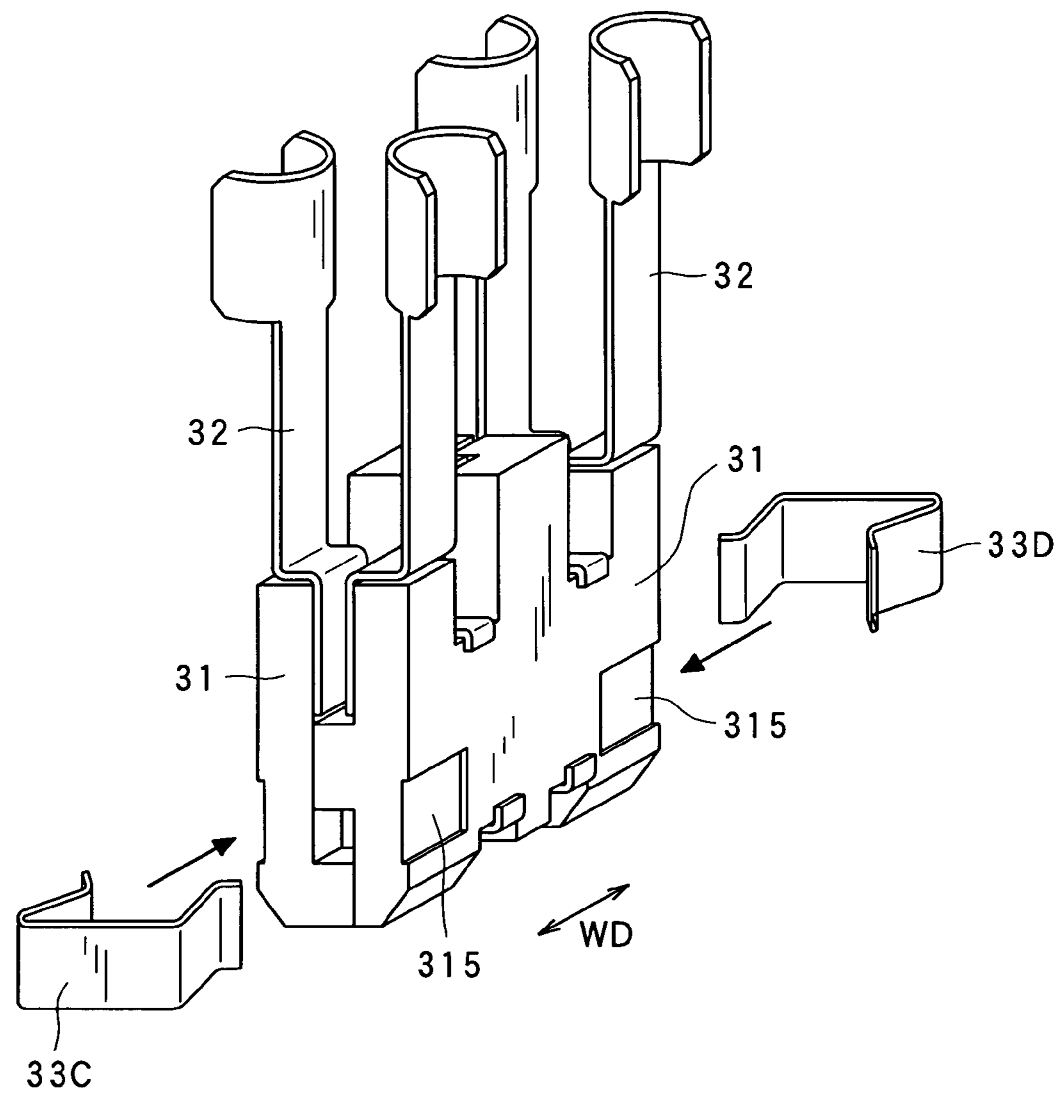
FIG. 20 is a perspective view showing a terminal unit and a spring member both of which are according to a third embodiment of the present invention.

Referring to FIG. 20, a gas sensor according to a third embodiment of the present invention will now be described.

In gas sensor according to the present embodiment, as shown in FIG. 20, the paired base-side insulators 31 of the terminal unit 3 are pressed by two mutually independent spring members 33C and 33D. In addition, the two spring members 33C and 33D are assembled with the insulators 31 from its sides so as to grip the insulators 31.

The remaining configurations in the third embodiment are the same as those in the first embodiment. The configurations in the third embodiment are thus able to provide the similar advantageous operations to those in the first embodiment.

(Fourth Embodiment)

Figure 21:
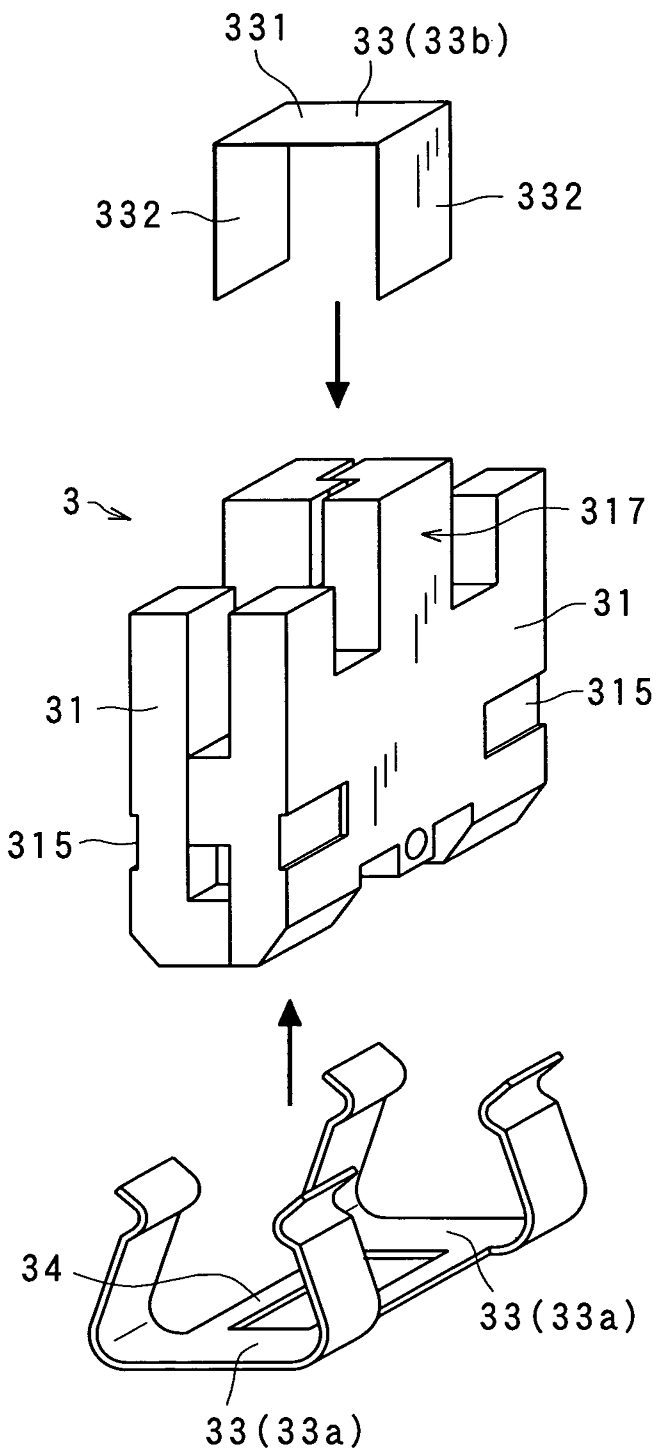
FIG. 21 is a perspective view showing a terminal unit and a spring member both of which are according to a fourth embodiment of the present invention.
Figure 22:
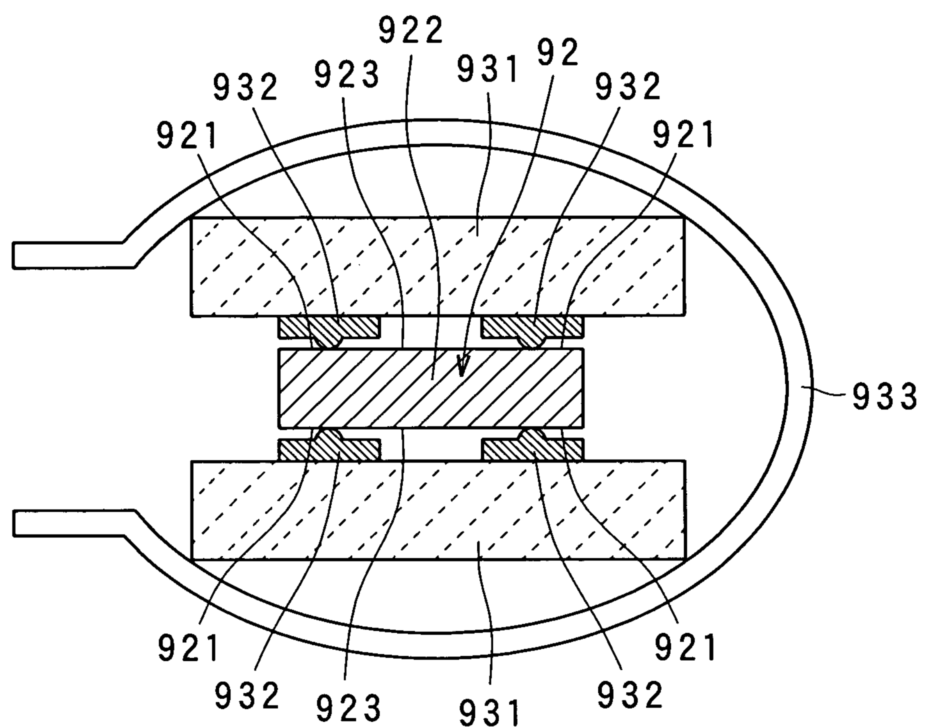
FIG. 22 is a sectional view showing a base-side insulator gripping a sensing element, which shows a conventional structure adopted by a conventional gas sensor.

Referring to FIG. 21, a gas sensor according to a fourth embodiment of the present invention will now be described.

As shown in FIG. 21, the paired base-side insulators 31 are pressed by a set of spring members 33*a* unified as a single member by a connecting member 34. Moreover, a further one spring member 33*b* is capped on the top of the paired base-side insulators 31.

Practically the paired base-side insulators 31 have an approximately quadratic-prism-shaped engaging protrusion 317 at the top of the mutually combined insulators 31. Further, the spring member 33*b* has a planar base part 331 and a pair of rising parts 332 respectively standing at a right angle from both edges of the planar base part 331.

In the present embodiment, the paired combined base-side insulators 31 is grasped by the set of spring members 33*a* from its lower end and also grasped by the spring member 33*b* at its engaging protrusion 317. Incidentally, in FIG. 21, the metal terminals 32 are omitted from being drawn.

The remaining configurations in the fourth embodiment are the same as those in the first embodiment. The configurations in the fourth embodiment are thus able to provide the similar advantageous operations to those in the first embodiment.

As an alternative example, the number of spring members 33 is not always limited to two in the width direction WD, but may be three or more. In such a case, the three or more spring members may either be combined into a sole device as shown in FIGS. 9, 19 and 21 or may be separate devices as shown in FIGS. 19 and 20.

The present invention may be embodied in several other forms without departing from the spirit thereof. The embodiments and modifications described so far are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensor comprising:

a sensing element with an axial direction which is set along a length direction thereof, a thickness direction perpendicular to the axial direction, and a width direction perpendicular to both the axial direction and the thickness direction when the gas sensor is assembled, and comprising (i) a base end portion located at one end of the sensing element in the axial direction, (ii) a cell composed of an oxygen ion conductive solid electrolyte member, (iii) a pair of electrode-mounted surfaces formed on both outer sides of the base end portion to be back to back in the thickness direction, to be parallel with each other, and to be perpendicular to the thickness direction, and (iv) a heater to heat the cell, the cell being integrally assembled with the heater;

a first insulator through which the sensing element is inserted to be held;

a housing fixedly containing the first insulator which is inserted through the housing;

two pairs of electrode pads secured on the pair of electrode-mounted surfaces of the base end portion of the sensing element so as to allow the two pairs of electrode pads to provide electrical connections for heating the cell and for detecting a concentration of a specific gas to be measured, pair by pair, wherein the two electrode pads belonging to each of the two pairs of electrode pads are disposed on the pair of electrode-mounted surfaces respectively such that the two electrode pads are distanced from each other in the width direction; and a terminal unit comprising a pair of second insulators, each insulator of the pair of second insulators having an inner side flat surface and an outer side surface with securing recesses, the pair of second insulators being disposed to pinch and hold both the electrode-mounted surfaces of the base end portion of the sensing element, two pairs of plate-shaped metal terminals electrically contacting the electrode pads, pair by pair, respectively, and being disposed on the inner side surfaces of the pair of second insulators, the two pairs of metal terminals and the pair of second insulators being aligned via the sensing element in the thickness direction, and a spring member formed to have a plurality of spring contact portions and arranged such that the spring contact portions of the spring member press the securing recesses of the pair of second insulators mutually inward from the securing recesses in the thickness direction at one or more different positions on each of the electrode-mounted surfaces in the width direction, the one or more different positions including two different positions on, at least, one of the electrode-mounted surfaces on both sides of the sensing element in the thickness direction, the two different positions being separated larger than a distance between the two metal terminals in the width direction and located respectively on both outsides of the two metal terminals in the width direction.

2. The gas sensor of claim 1, wherein the spring member is composed of a plurality of pairs of spring members unified by a connecting member, each pair of the plurality of pairs of spring members having the spring contact portions which press the securing recesses of the pair of the second insulators mutually inwardly in the thickness direction at the same position in the width direction.

3. The gas sensor of claim 2, wherein the spring member is composed of two pairs of spring members unified by a connecting member, each pair of the two of pairs of spring members having the spring contact portions which press the securing recesses of the pair of the second insulators mutually inwardly in the thickness direction at the same position in the width direction.

4. The gas sensor of claim 3, wherein each second insulator of the pair of second insulators has an insulative protrusion that protrudes toward the sensing element, each metal terminal of each pair of the two pairs of plate-shaped metal terminals has a protruding contact part that contacts a corresponding electrode pad of the two electrode pads at a first position in the axial direction, the first position where the protruding contact part contacts the corresponding electrode pad is shifted in the axial direction from a second position where the insulative protrusion contacts the sensing element in the axial direction, the first and second positions in the axial direction also being the different positions on each of the electrode-mounted surfaces in the width direction.

5. The gas sensor of claim 2, wherein each second insulator of the pair of second insulators has an insulative protrusion that protrudes toward the sensing element, each metal terminal of each pair of the two pairs of plate-shaped metal terminals has a protruding contact part that contacts a corresponding electrode pad of the two electrode pads at a first position in the axial direction, the first position where the protruding contact part contacts the corresponding electrode pad is shifted in the axial direction from a second position where the insulative protrusion contacts the sensing element in the axial direction, the first and second positions in the axial direction also being the different positions on each of the electrode-mounted surfaces in the width direction.

6. The gas sensor of claim 5, wherein the terminal unit is provided with a plurality of recesses opened from sides thereof, the recesses being opened along different two directions which are perpendicular to the axial direction of the sensing element and parallel with the electrode-mounted surfaces of the sensing element.

7. The gas sensor of claim 1, wherein the terminal unit is provided with a plurality of recesses opened from sides thereof, the recesses being opened along different two directions which are perpendicular to the axial direction of the sensing element and parallel with the electrode-mounted surfaces of the sensing element.

8. The gas sensor of claim 1, wherein the spring member has two pairs of pressing portions which press the securing recesses of the pair of second insulators mutually inward in the thickness direction.

9. The gas sensor of claim 1, wherein the spring member is composed of two spring members each having two pressing portions pressing the securing recesses of the pair of second insulators mutually inward in the thickness direction at the same position on the electrode-mounted surfaces in the width direction.

10. A method of manufacturing a gas sensor set forth in claim 1, the manufacturing method comprising steps of:

separating the pair of second insulators by applying a separating force against a pressure force of the spring member until there is formed a gap between the two pairs of metal terminals, the gap being larger than a thickness between the electrode-mounted surfaces of the base end portion of the sensing element;

inserting the base end portion of the sensing element into the gap; and releasing the separating force so that, with the two pairs of metal terminals made to contact the electrode pads, the base end portion of the sensing element is fixedly gripped by the terminal unit.

* * * * *